United States Patent
Munn

(10) Patent No.: US 7,946,289 B2
(45) Date of Patent: *May 24, 2011

(54) ORAL AIRWAY

(76) Inventor: Myron L. Munn, Beatrice, NE (US)

(*) Notice: Subject to any disclaimer, the term of this patent is extended or adjusted under 35 U.S.C. 154(b) by 928 days.

This patent is subject to a terminal disclaimer.

(21) Appl. No.: 11/584,980

(22) Filed: Oct. 23, 2006

(65) Prior Publication Data

US 2008/0092882 A1 Apr. 24, 2008

(51) Int. Cl.
*A61M 16/00* (2006.01)
*A62B 9/06* (2006.01)

(52) U.S. Cl. .............. 128/200.26; 128/207.14

(58) Field of Classification Search ............ 128/207.14, 128/200.24, 200.26, 204.18, 207.15–207.17
See application file for complete search history.

(56) References Cited

U.S. PATENT DOCUMENTS

| | | | |
|---|---|---|---|
| 2,127,215 A | 8/1938 | Gwathmey | |
| 2,599,521 A | 6/1952 | Berman | |
| 2,705,959 A | 4/1955 | Elmore | |
| 3,306,298 A | 2/1967 | Raimo | |
| 3,398,747 A | 8/1968 | Raimo | |
| 3,419,004 A * | 12/1968 | Berman | 128/207.14 |
| 3,543,751 A * | 12/1970 | Sheffer | 128/207.15 |
| 3,568,680 A | 3/1971 | Raimo | |
| 3,576,187 A | 4/1971 | Oddera | |
| 3,756,244 A | 9/1973 | Kinnear et al. | |
| 3,908,665 A | 9/1975 | Moses | |
| 3,926,196 A | 12/1975 | Bornhorst et al. | |
| 3,930,507 A | 1/1976 | Berman | |
| D261,442 S | 10/1981 | Anderson | |
| 4,363,320 A | 12/1982 | Kossove | |
| 4,553,540 A * | 11/1985 | Straith | 128/200.26 |
| 4,919,126 A | 4/1990 | Baildon | |
| 6,196,224 B1 | 3/2001 | Alfery | |
| 6,679,901 B1 * | 1/2004 | Takuma | 606/196 |
| 6,901,928 B2 * | 6/2005 | Loubser | 128/200.26 |
| 6,918,388 B2 * | 7/2005 | Brain | 128/200.26 |
| 2004/0129272 A1 * | 7/2004 | Ganesh et al. | 128/207.14 |
| 2005/0016531 A1 * | 1/2005 | Takuma | 128/200.26 |
| 2007/0267024 A1 * | 11/2007 | Kremer et al. | 128/207.14 |
| 2008/0092900 A1 * | 4/2008 | Munn | 128/207.14 |
| 2008/0185004 A1 * | 8/2008 | Munn | 128/207.14 |

* cited by examiner

*Primary Examiner* — Justine R Yu
*Assistant Examiner* — Rachel T Young
(74) *Attorney, Agent, or Firm* — Dennis L. Thomte; Thomte Patent Law Office LLC

(57) ABSTRACT

An oral airway for providing an air passage to a patient's trachea including two embodiments. In both embodiments, the oral airway includes a curved section and a straight section with the curved section having spaced-apart curved upper and lower members and the straight section having spaced-apart planar upper and lower members with the same width. In the first embodiment, the curved upper member has the same width as the planar upper member with the curved lower member having a greater width than the width of the lower planar member. In the second embodiment, the width of the curved lower member is greater than the width of the planar lower member and the distance between the curved upper and lower members is greater than the distance between the planar upper and lower members.

2 Claims, 4 Drawing Sheets

ORAL AIRWAY

BACKGROUND OF THE INVENTION

1. Field of the Invention

This invention relates to an oral airway and more particularly to an oral airway which truly represents an improvement in the oral airway art.

2. Description of the Related Art

In modern anesthesia practice, oral airways are used primarily for two reasons. The first reason is that after intubation of the trachea, an oral airway is placed to prevent a patient from biting down on the endotracheal tube and thus occluding the endotracheal tube. The second and primary reason for the use of an oral airway in the practice of anesthesia is to elevate the tongue against the floor of the mouth to create a larger opening in the mouth to facilitate the utilization of positive pressure ventilation using an anesthesia mask after a patient has been given medications to induce general anesthesia. The drugs normally used to induce general anesthesia may greatly decrease or altogether stop the patient's own spontaneous respiratory effort. Therefore, the Anesthesia Practitioner must immediately begin assisting or controlling the patient's ventilation.

It has been noted that patients undergoing general anesthesia have occasional difficulties in maintaining the patient's airway and the ability to ventilate the patient. It has been observed that patients of all ages were difficult to ventilate with an anesthesia mask after induction of general anesthesia. This has happened even after proper placement of the recommended size of oral airway. Anyone who has practiced anesthesia for some time has experienced the same difficulties. Anesthesia Practitioners are all taught the "tricks of the trade" in how to ventilate patients after induction of general anesthesia including a variety of physical adjustments to the anesthetized patient such as elevation of the jaw and extension of the patient's neck. If the patient cannot be adequately ventilated after induction of general anesthesia, life-threatening problems may develop such as hypoxia, hypercarbia, cardiac arrhythmias and even death.

Once general anesthesia has been induced, one of the main impediments to adequately ventilating a patient with positive pressure ventilation, after placement of an oral airway, is the relaxation of the soft tissue structures in the hypo-pharynx. These structures tend to collapse, thus obstructing airflow. This inward collapsing occurs both front to back and side to side, thus greatly decreasing the size of the oral opening through which the Anesthesia Practitioner may ventilate the patient. This anatomical relaxation is fairly consistent with every patient who undergoes a general anesthetic. However, there is a physical characteristic of some patients which greatly increases the difficulty of mask ventilation—that characteristic is obesity. Applicant has noted the increasing incidence of obesity in both the pediatric and adult population. These obese patients present an increased level of difficulty to the Anesthesia Practitioner in the area of airway management. Obese patients tend to have larger, thicker tongues along with more redundant soft tissue in the oropharyngeal area. Obese patients also tend to have thicker necks, so it is more difficult to hyperextend the neck and lift the jaw to facilitate adequate ventilation after general anesthesia is induced. In discussions with Anesthesia Practitioners, the inventor has perceived a common concern that the oral airways currently available do not adequately address the growing problem of obesity in the population.

As stated, it is well known to utilize an oral airway for the purpose of aiding the breathing of unconscious patients. Reference may be made to U.S. Pat. No. 2,599,521, which issued Jun. 3, 1952, to R. A. Berman, for a description of a conventional oral airway now known in medical practice as the Berman Oral Airway. The Berman Oral Airway, and later devices modeled after it, is employed in the practice of anesthesia and other areas of respiratory medicine by insertion of the oral airway into the mouth and pharynx of a patient to provide a channel for respiratory purposes, particularly in unconscious patients such as those who have been administered a general anesthetic. It is the purpose of the oral airway to prevent respiratory obstruction by preventing collapse of the pharyngeal tissues and/or obstruction of the pharynx by the tongue.

The Berman Oral Airway and later devices are available to the medical professional in a number of different sizes for use in all sizes of patients from premature infants to large adults. However, each size constitutes a unitary member which may not itself be adjusted in size, shape, or contour. Thus, conventional airways are substantially rigid structures which may not be altered in use to fit particular patients, particular problems, or unusual anatomic anomalies or structures. The Berman Oral Airway has served Anesthesia Practitioners well for many years, but the physical characteristics of patients have changed since 1952 while the Berman Oral Airway remains the same.

The Berman Oral Airway comes in various sizes from 40 mm to 100 mm in incremental steps of 10 mm (i.e., 40 mm, 50 mm, 60 mm, 70 mm, 80 mm, 90 mm, and 100 mm). These sizes are roughly correlated to general anatomic dimension described as the distance from the exterior of the front teeth to the back of the oropharynx. So, correspondingly, a 40 mm Berman Oral Airway is probably an appropriate size for a premature infant whereas a 100 mm Berman Oral Airway is probably appropriate for a large adult, and a 90 mm Berman Oral Airway is generally used on a medium adult patient. If the patient is very obese and has a thick tongue and has a large amount of soft tissue in the oropharynx, the 90 mm oral airway may not adequately elevate the tongue because it is not wide enough side to side to provide enough support for the tongue. In this case, a 100 mm Berman Oral Airway (which is wider side to side) may provide the additional support for the tongue that is needed to open the airway, but it cannot be used because the longer structure of the airway (100 mm) may not fit in the patient's mouth. The 100 mm oral airway would extend too far outside of the patient's mouth, thus placing an anesthesia mask over the patient's face to obtain a good mask seal in order to ventilate the patient with positive pressure would be very difficult, if not impossible. The usual scenario is someone who is of very short stature and very obese. These people many times need the width and depth of a 100 mm Berman Oral Airway, but the length of an 80 mm Berman Oral Airway. This would greatly facilitate the ability to ventilate this patient after induction of general anesthesia. This problem has been overcome in the past by actually inserting two 80 mm Berman Oral Airways on these types of patients or sometimes one 90 mm Berman Oral Airway and one 80 mm Berman Oral Airway. In this way you are able to achieve enough side to side tongue support to adequately ventilate the patient until you are ready to place an LMA or intubate the patient. Inserting two airways into the patient is sometimes adequate but can be awkward. Therefore, a new type of airway is needed for these patients.

SUMMARY OF THE INVENTION

The Munn Oral Airway

Accordingly, the present invention provides modifications to the Berman Oral Airway which will provide better elevation of the tongue against the floor of the mouth by way of: 1) a longer middle support distance which increases the distance the tongue is elevated against the floor of the mouth thus increasing the anterior-posterior dimension of the airway opening; and 2) the greater width of the curved lower member of the curved section of the oral airway which will give better support to the tongue laterally, thus increasing the side-to-side dimension of the airway opening.

By altering these two dimensions of the Berman Oral Airway, but not altering the length or the radius of the curve of the airway, the Munn oral airway sizes would be interchangeable with the Berman Oral Airway sizes. For instance, in a situation where you would normally use an 80 mm Berman Oral Airway, the 80 mm airway of this invention would be appropriate, but would give better tongue support and consequently a larger opening of the patient's airway to facilitate easier ventilation of the patient. This would be especially helpful in obese patients with large tongues, but would also be useful for all patients being administered general anesthesia.

More particularly, the oral airway of this invention comprises a straight section having inner and outer ends adapted to fit between the patient's teeth and a curved section adapted to fit over the patient's tongue and extending to the oropharyngeal area. The straight section of the oral airway includes a substantially planar upper member and a substantially planar lower member which are spaced-apart by a medial web extending therebetween. The planar upper and lower members of the straight section have substantially the same widths. The outer end of the planar upper member has an upwardly extending flange provided thereon and the outer end of the planar lower member has a downwardly extending flange provided thereon with the flanges externally overlying the lips of the patient. The curved section of the oral airway comprises spaced-apart curved upper and lower members which are spaced-apart by a medial web extending therebetween. The curved upper member of the curved section has substantially the same width as the planar upper member of the straight section. The curved lower member of the curved section has a greater width for substantially its entire length than the planar lower member of the straight section. In a modified version of the oral airway described above, the distance between the curved upper and lower members of the curved section, for substantially the entire length thereof, is greater than the distance between the planar upper and lower members of the straight section. The oral airway of this invention may be either a 100 mm, 90 mm, 80 mm, 70 mm, 60 mm, 50 mm, or 40 mm size.

It is therefore a principal object of the invention to provide an improved oral airway to provide an air passage to the patient's trachea.

A further object of the invention is to provide an improved oral airway which will provide better elevation of the tongue against the floor of the mouth by way of: 1) a longer middle support distance which increases the distance the tongue is elevated against the floor of the mouth, thus increasing the anterior-posterior dimension of the airway opening; and 2) the greater width of the curved lower member of the curved section of the oral airway which will give better support to the tongue laterally, thereby increasing the side-to-side dimension of the airway opening.

These and other objects will be apparent to those skilled in the art.

DETAILED DESCRIPTION OF THE INVENTION

Figure 2:
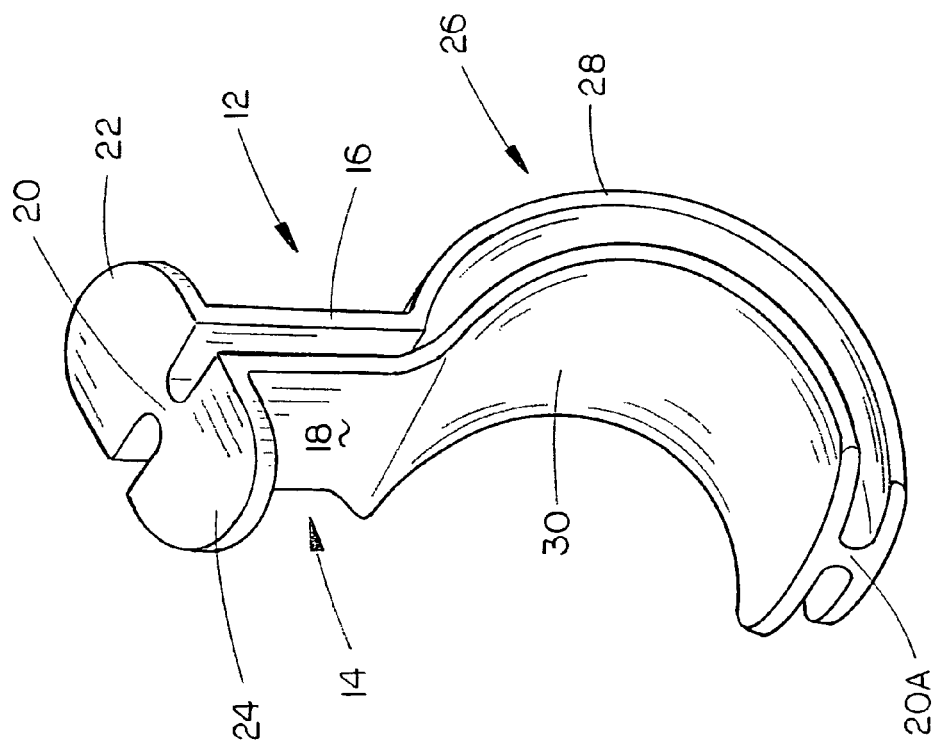
FIG. 2 is a perspective view of a larger oral airway of this invention.
Figure 1:
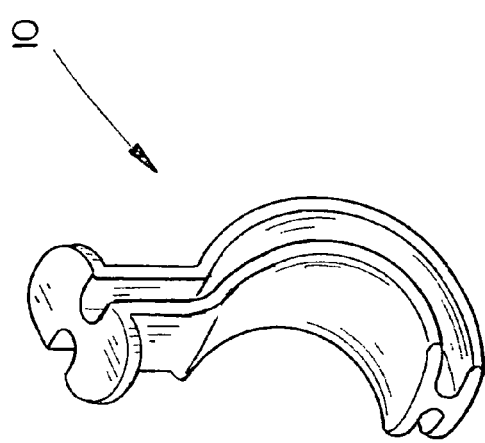
FIG. 1 is a perspective view of a smaller oral airway of this invention.

In FIG. 1, the numeral 10 refers generally to one embodiment of this invention and which is a smaller version of the airway such as a 50 mm airway. In FIG. 2, the numeral 12 refers to a larger airway of the same configuration as the airway 10 except that it is a 90 mm or 100 mm airway. Inasmuch as the structure of the airways 10 and 12 are identical, only airway 12 will be described in detail.

Airway 12 includes a straight section 14 having an upper planar member 16 and a lower planar member 18 which are spaced-apart by means of a medial web or rib 20. Flange 22 extends upwardly from the outer end of planar upper member 16 while flange 24 extends downwardly from the outer end of planar lower member 18. The flanges 22 and 24 externally overlie the lips of the patient as illustrated generally in FIG. 3 except that a modified form of the airway is disclosed as will be described hereinafter.

Airway 12 also includes a curved section 26 which is comprised of a curved upper member 28 and a curved lower member 30 which are spaced-apart by a continuation of the medial web 20 and which is designated by the reference numeral 20A. The width of upper member 28 is substantially the same as the width of the planar upper member 16. The width of curved lower member 30 is greater than the width of planar lower member 18 and greater than the width of member 28. In the embodiment of FIG. 2, the members 28 and 30 are spaced-apart a distance which is equal to the distance between members 16 and 18.

Figure 3:
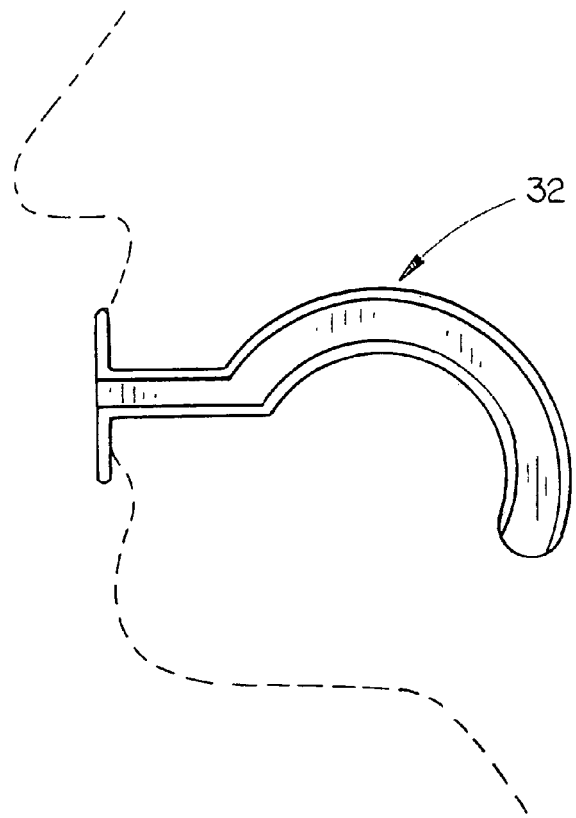
FIG. 3 is a side view of the oral airway of this invention inserted into a patient.
Figure 4:
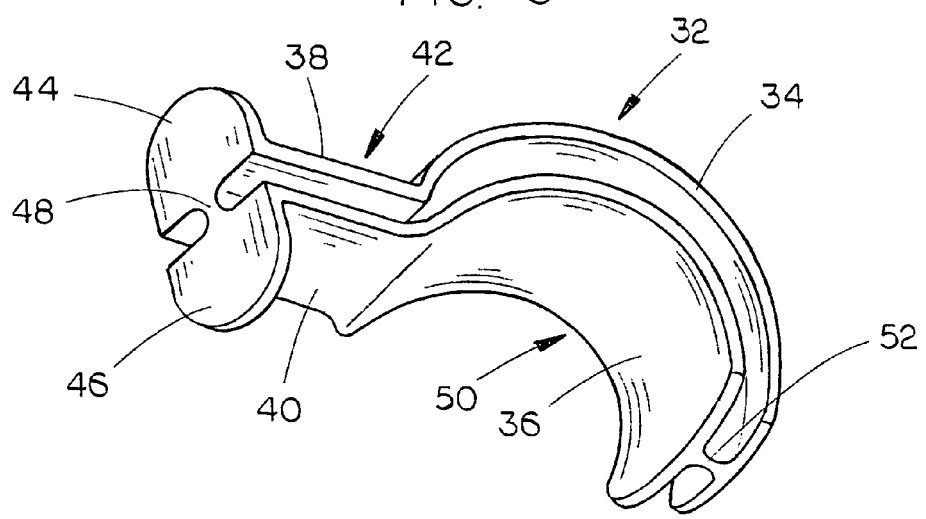
FIG. 4 is a perspective view of an oral airway of this invention similar to that of FIG. 2 except that the curved upper and lower members of the curved section of the airway are spaced farther apart than that of FIG. 2.

Referring now to FIG. 3, a modified version of the airway shown in FIGS. 1 and 2 is illustrated and is referred to generally by the reference numeral 32. The only difference between the airway 12 and the airway 32 is that the spacing between the curved upper member 34 and the curved lower member 36 is greater than the distance between the planar upper member 38 and the planar lower member 40 of the straight section 42. Oral airway 32 also includes flanges 44 and 46 spaced-apart by a medial web or rib 48. As seen in FIG. 4, the curved members 34 and 36 of curved section 50 are spaced-apart by the medial web or rib 52. As in airway 12, the width of upper member 34 is approximately the same as the width of planar upper member 38 and the width of curved lower member 36 is greater than the width of the planar lower member 40.

Figure 6:
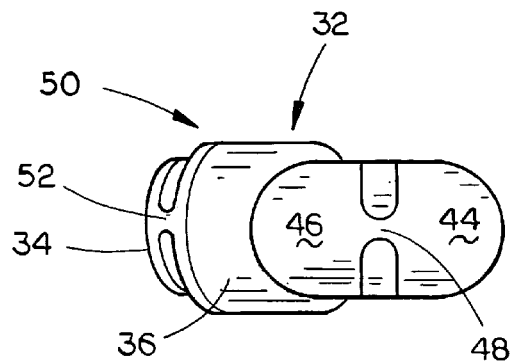
FIG. 6 is a top view of the oral airway of FIG. 5.
Figure 5:
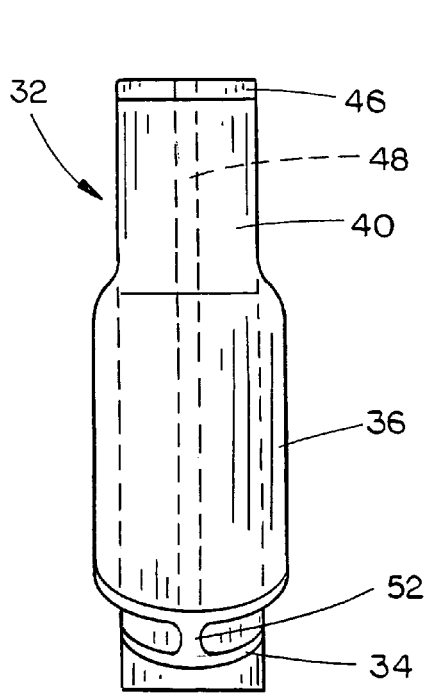
FIG. 5 is a bottom elevational view of the airway of FIG. 4.
Figure 7:
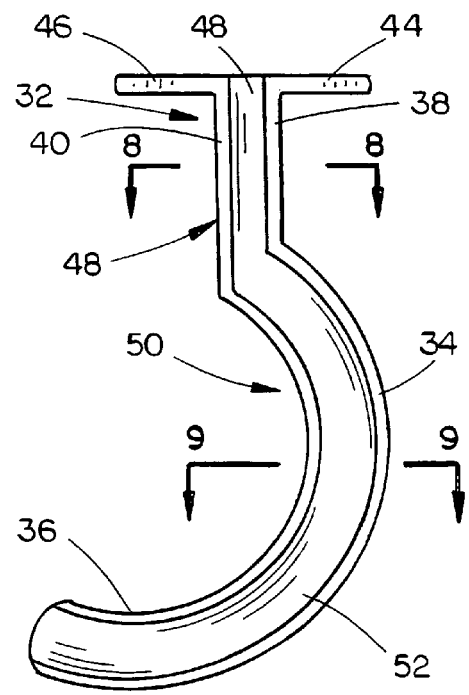
FIG. 7 is a side view of the oral airway of FIG. 5.
Figure 8:
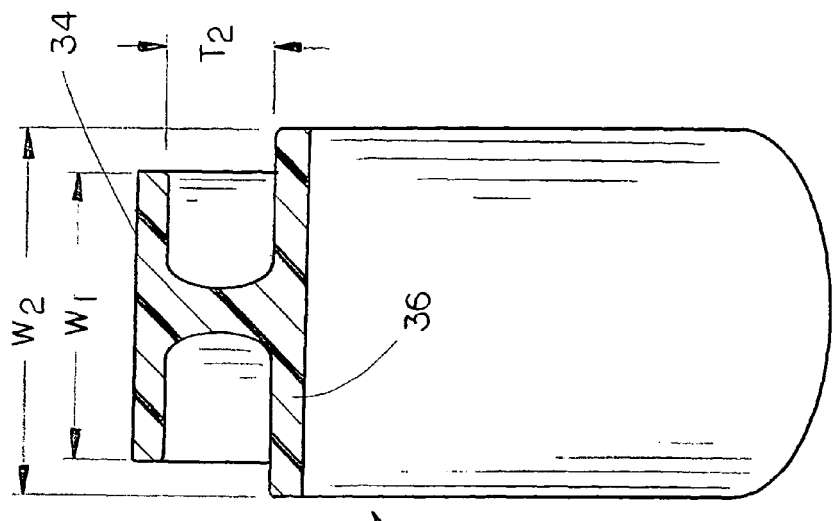
FIG. 8 is a sectional view as seen on lines 8-8 of FIG. 7.

FIG. 5 is a bottom elevational view with FIG. 6 being a top and end view, as seen from the outer end of the airway 32. FIG. 7 illustrates a side view of the oral airway pictured in FIG. 4. FIG. 8 illustrates a cross-sectional view of the straight section 42 of the oral airway 32 wherein it can be seen that the width $W_1$ of the members 38 and 40 is less than the width of the curved lower member 36.

Figure 9:
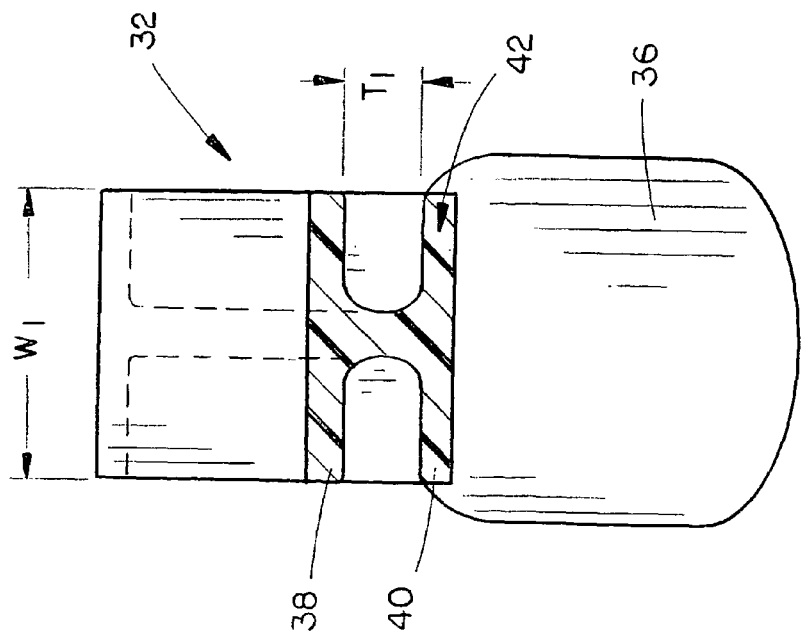
FIG. 9 is a sectional view as seen on lines 9-9 of FIG. 7.

Comparing FIG. 8 to FIG. 9, it can be seen that the width of lower member 36 is greater than the width of the upper member 34 and that the width $W_1$ of the upper member 34 is the same as the width $W_1$ of the planar upper and lower members 38 and 40 of straight section 42.

Thus it can be seen that two different embodiments of the oral airway of this invention are illustrated, that is, 1) the oral airway 12 of FIG. 2 wherein the curved lower member 30 has a width greater than the width of the curved upper member 28 with the space between members 28 and 30 being increased compared to the space between the planar upper and lower members 16 and 18 of the straight section 14; and 2) the oral airway 32 of FIGS. 3-9 wherein the airway has a curved lower member 36 which has a width greater than the width of the curved upper member 34 with the space between members 34 and 36 being greater than the space between the members 38 and 40 of straight section 42.

Chart A reproduced hereinbelow illustrates the approximate widths of various sizes of the Berman Oral Airway and the various depths of the Berman Oral Airway. The widths illustrated in Chart A illustrate the approximate widths of the distance $W_1$ (see FIGS. 8 and 9) of the Berman Oral Airway while the depth illustrated in Chart A is representative of the approximate distances (depth) between the upper and lower members of the straight and curved sections of the Berman Oral Airway.

CHART A

| MILLIMETERS | WIDTH | DEPTH |
| --- | --- | --- |
| 100 | 21.8 mm | 9.4 mm |
| 90 | 19.6 mm | 8.6 mm |
| 80 | 17.0 mm | 7.8 mm |
| 70 | 15.2 mm | 7.5 mm |
| 60 | 13.3 mm | 6.9 mm |
| 50 | 12.8 mm | 5.55 mm |
| 40 | 9.7 mm | 4.85 mm |

Chart B is a chart representing the various widths of the curved lower member and depths of various sizes of the oral airway of this invention (airway 32) and it can be seen that the airways of Chart B provide a greater width of the curved lower member 36 of airway 32 than does the comparable Berman Oral Airway, thus increasing the amount of surface structure of the oral airway to lift the tongue for easier ventilation of the patient. It can also be seen in Chart B that the depth (space) between the upper and lower members of the curved section 50 of the airway 32 results in a greater depth or space therebetween thereby increasing the distance the tongue is elevated.

CHART B

| MILLIMETERS | WIDTH | DEPTH |
| --- | --- | --- |
| 100 | 28.4 mm | 11.3 mm |
| 90 | 25.5 mm | 10.4 mm |
| 80 | 22.1 mm | 9.4 mm |
| 70 | 19.7 mm | 9.0 mm |
| 60 | 17.3 mm | 8.3 mm |
| 50 | 16.6 mm | 6.7 mm |
| 40 | 12.6 mm | 5.8 mm |

Therefore, the present invention provides modifications to the Berman Oral Airway which will provide better elevation to the tongue against the floor of the mouth by way of: 1) the longer middle support distance which increases the distance the tongue is elevated against the floor of the mouth thus increasing the anterior-posterior dimension of the airway opening; and 2) the greater width of the lower member 36 which will give better support to the tongue laterally, thus increasing the side-to-side dimension of the airway opening.

By altering the two dimensions of the Berman Oral Airway, but not altering the length or the radius of the curve of the airway, the size of the oral airway of this invention would be interchangeable with the Berman Oral Airway sizes. For instance, in a situation wherein a person would normally use an 80 mm Berman Oral Airway, the 80 mm airway of this invention would be appropriate, but would give better tongue support and consequently a larger opening of the patient's airway to facilitate easier ventilation of the patient. This would be especially helpful in obese patients with large tongues, but would also be useful for all patients being administered general anesthesia.

Thus it can be seen that the invention accomplishes at least all of its stated objectives.

I claim:

1. An oral airway to provide an air passage to a patient's trachea, comprising:

a straight section having inner and outer ends adapted to fit between the patient's teeth;

a curved section having inner and outer ends adapted to fit over the patient's tongue and extending to the oropharyngeal area;

said straight section including a substantially planar upper member and a substantially planar lower member which are spaced-apart by a medial web extending therebetween;

said planar upper and lower members having inner and outer ends;

said planar upper and lower members of said straight section having substantially the same widths;

said outer end of said planar upper member having a flange extending upwardly therefrom;

said outer end of said planar lower member having a flange extending downwardly therefrom;

said flanges adapted to be externally overlying the lips of the patient;

said curved section comprising spaced-apart curved upper and lower members which are spaced-apart by a medial web extending therebetween;

said curved upper and lower members having inner and outer ends;

said curved lower member having substantially the same width for its entire length between the inner and outer ends thereof;

said curved upper member of said curved section having substantially the same width as said planar upper member of said straight section;

said curved lower member of said curved section having a greater width for substantially its entire length between the inner and outer ends thereof than said planar lower member of said straight section and said curved upper member.

2. The oral airway of claim 1 wherein the distance between said curved upper and lower members of said curved section, for substantially the entire length between the inner and outer ends thereof, is greater than the distance between said planar upper and lower members of said straight section.

* * * * *